United States Patent [19]

Friedow et al.

[11] Patent Number: 5,683,151
[45] Date of Patent: Nov. 4, 1997

[54] HYDRAULIC UNIT FOR TRACTION-CONTROLLED MOTOR VEHICLE BRAKE SYSTEMS

[75] Inventors: Michael Friedow, Tamm; Jurgen Lander, Stuttgart; Helmut Staib, Schwieberdingen; Klaus Mueller, Tamm, all of Germany

[73] Assignee: Robert Bosch GmbH, Stuttgart, Germany

[21] Appl. No.: 617,932

[22] PCT Filed: Sep. 21, 1994

[86] PCT No.: PCT/DE94/01098

§ 371 Date: Jun. 12, 1996

§ 102(e) Date: Jun. 12, 1996

[87] PCT Pub. No.: WO95/08462

PCT Pub. Date: Mar. 30, 1995

[30] Foreign Application Priority Data

Sep. 24, 1993 [DE] Germany .......... 43 32 538.6

[51] Int. Cl.⁶ .......... B60T 8/36; F15B 13/044; F16K 31/06
[52] U.S. Cl. .......... 303/119.2; 303/113.1; 303/900
[58] Field of Search .......... 303/119.2, 119.1, 303/113.1, 900, 901; 137/596.17; 251/129.15–129.22

[56] References Cited

U.S. PATENT DOCUMENTS

| | | |
|---|---|---|
| 4,312,380 | 1/1982 | Leiber et al. |
| 5,324,134 | 6/1994 | Kaes et al. .......... 403/282 |
| 5,335,984 | 8/1994 | Alaze et al. .......... 303/119.2 |
| 5,374,116 | 12/1994 | Burgdorf et al. .......... 303/113.1 |

FOREIGN PATENT DOCUMENTS

| | | |
|---|---|---|
| 526440 | 1/1993 | European Pat. Off. .......... 303/119.2 |
| 3810581 | 10/1989 | Germany . |
| 4030571 | 4/1992 | Germany . |
| 4142004 | 6/1993 | Germany . |
| 4330616 | 3/1994 | Germany . |
| 04151080 | 5/1992 | Japan . |
| 9117378 | 11/1991 | WIPO . |
| 9212878 | 8/1992 | WIPO . |

OTHER PUBLICATIONS

Patent Abstracts of Japan, vol. 16, No. 438 (M–1309) 11 Sep. 1992.

Primary Examiner—Douglas C. Butler
Attorney, Agent, or Firm—Edwin E. Greigg; Ronald E. Greigg

[57] ABSTRACT

The object is to reduce the weight of the hydraulic unit. The hydraulic unit (12) has a metal valve block (11) with at least one stepped receiving bore (15) for the hydraulic portion of an electromagnetically actuated valve (10). The hydraulic portion (13) is provided with a securing flange (30), which is inserted into a step (46) of the receiving bore (15) and is positionally secured by a caulking (48) formed from the metal of the valve block (11). A valve dome (16) protruding beyond the boundary plane (17) of the valve block (11) carries the electric portion (14) of the valve (10). The savings in weight is attained by using light metal, such as an aluminum alloy or the like, for the valve block (11). The hydraulic unit is intended for traction-controlled brake systems of motor vehicles.

5 Claims, 2 Drawing Sheets

HYDRAULIC UNIT FOR TRACTION-CONTROLLED MOTOR VEHICLE BRAKE SYSTEMS

BACKGROUND OF THE INVENTION

The invention is based on a hydraulic unit for traction-controlled brake systems of motor vehicles, as generically defined by the preamble to the main claim.

German Patent Application DE 38 10 581 A1 has already disclosed making such a hydraulic unit with a valve block from steel, making stepped receiving bores for the hydraulic portion of electromagnetically actuated valves in the block, providing securing flanges for the valves, introducing the flanges into the stepped bores, and caulking the steel material of the valve block against the securing flanges in order to positionally secure the valves in a pressure-tight manner. DE 38 10 581 A1 expressly points out that the caulking process makes it indispensible that only steel be used as the material. It says that this makes such hydraulic units heavy and makes the caulking expensive and not without problems, especially with respect to the sealing. Instead, for a light structure of aluminum, it proposes fastening at least one electromagnet valve between two aluminum plates by means of tension screws. In the state of the art that is discussed in DE 38 10 581 A1 as being disadvantageous, the securing flange of the applicable electromagnet valve is made by funnel-like flaring of the open end of a capsule-like valve dome which contains magnetically operative elements, such as the armature and magnet core. Depending on the shape of the securing flange, the counterpart face of the step of the receiving bore is embodied expensively. The material of the valve block positively displaced by the caulking surrounds the entire circumference of the securing flange. Nevertheless, this embossed connection clearly does not meet the demands made of it in terms of strength, because German Patent Application DE 40 30 571 A1 describes letting a bushing, adapted to the shape of the securing flange, into the receiving bore of the valve block and providing not only the frictionally engaged fastening of the flange attained by the embossed connection but also a positive connection, so as to counteract the thrust force acting between the contact faces of the aforementioned elements. However, this makes it more expensive to secure the hydraulic part of the electromagnet valve in the valve block.

In electromagnetically actuated valves for brake systems of the type described at the outset, known from German Patent Application DE 41 42 004 A1, the valve dome has a radially protruding securing flange, which is retained in sealed fashion in a valve block by means of a screw sleeve slipped onto the valve dome. Securing in this way, by means of the screwed sleeve and an insertion thread disposed for it in the valve block, is expensive. Moreover, such insertion threads are harder to clean than smooth stepwise recessing of the diameter of bores. Yet careful cleaning is indispensible, because unremoved chips cause leakage between the securing flange and the valve block or can get into the hydraulic circuit, which can result in severe damage or loss of function of the hydraulic unit.

ADVANTAGES OF THE INVENTION

The hydraulic unit according to the invention as defined by the body of the main claim has the advantage over the prior art that not only can the at least one valve be connected to the valve block in a way that can be achieved economically, but also a considerable savings in weight is attained because of the choice of material which is substantially lighter than steel.

By the provisions recited in the dependent claims, advantageous further features of and improvements to the hydraulic unit defined by the main claim are possible.

With the embodiment defined by claim 2, on the one hand a diversion of forces acting upon the hydraulic portion of the valve to the valve block is attained in a simple way; on the other, deformation of the valve dome is avoided, and the freedom of motion of the elements disposed inside the valve dome is reinforced by the shaping of the bushing and by caulking of the securing flange, which can be done in an intrinsically arbitrary way.

The further feature defined by claim 3 is distinguished not only by less-complicated production of the receiving bore and securing flange but also by a connection between the hydraulic part of the valve and the valve block that is predominantly in the form of positive engagement and can withstand heavy loads.

With the improvement of claim 4, because of the material comprising the bushing, on the one hand high design strength of the bushing when its securing flange is caulked is attained, and on the other, favorable conduction of the magnetic flux between the housing of the electrical portion and the magnetically operative elements of the hydraulic portion of the valve is attained. Hence the bushing has dual utility.

DRAWING

Two exemplary embodiments of the invention are shown in simplified form in the drawing and are described in further detail below. FIG. 1 is a longitudinal section through an electromagnetically actuated valve that is closed when without current and is connected by an embossed connection to a valve block of a hydraulic unit; and FIG. 2 is a corresponding view of a valve which is open when without current.

DESCRIPTION OF THE EXEMPLARY EMBODIMENTS

Figure 1:
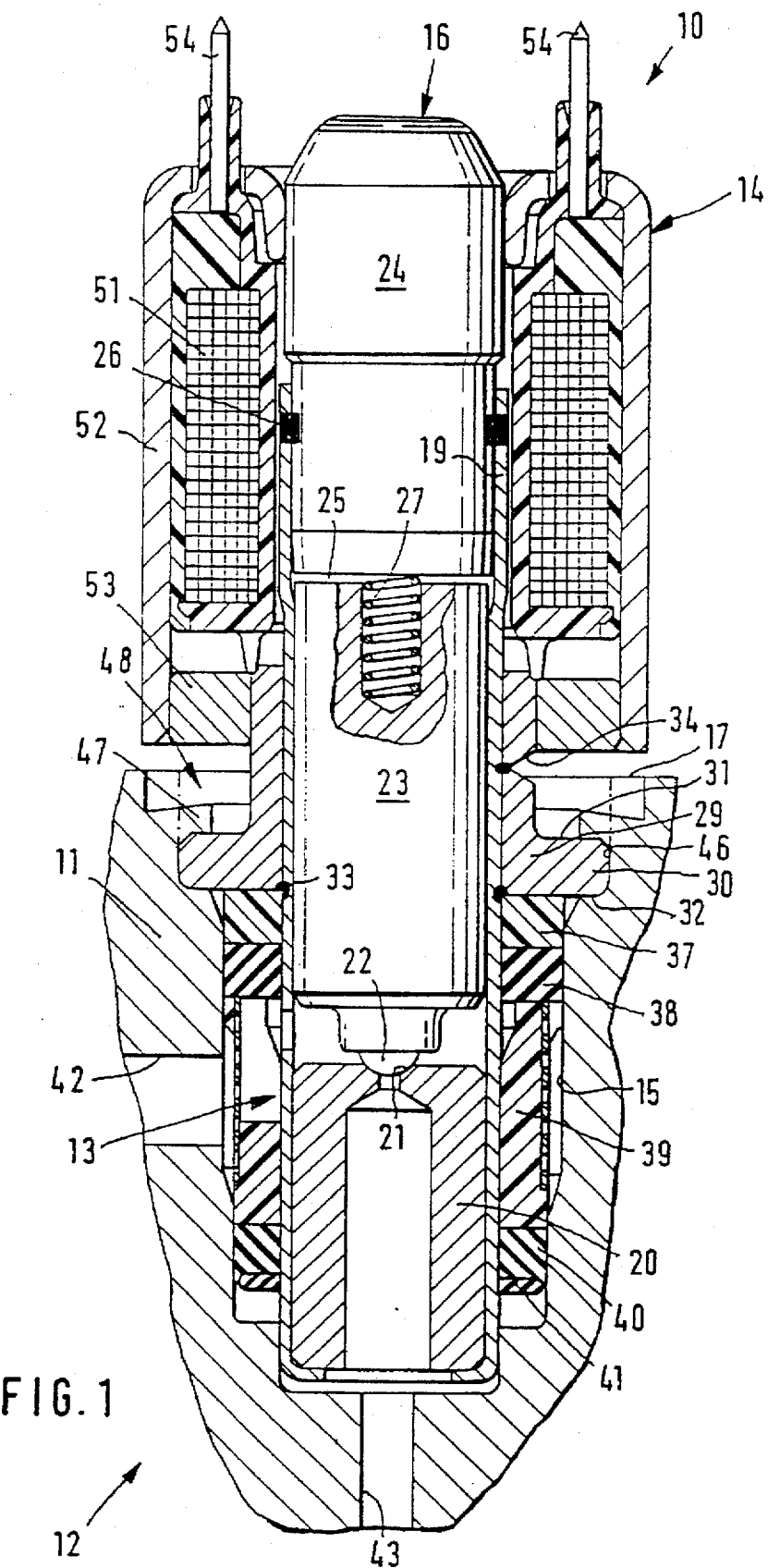

An electromagnetically actuated valve 10 shown as a first exemplary embodiment in FIG. 1 is disposed on a valve block 11 and forms a portion of a hydraulic unit 12, otherwise not shown, for traction-controlled brake systems of motor vehicles. The valve 10 comprises a hydraulic portion 13 and an electric portion 14. The hydraulic portion 13 is substantially received and secured in a stepped receiving bore 15 of the valve block 11, which is made from a ductile aluminum alloy. In the extension of the receiving bore 15, the hydraulic portion 13, with a valve dome 16, protrudes beyond a boundary plane 17 of the valve block 11. The electrical portion 14 is mounted on the valve dome 16.

The hydraulic portion 13 has a thin-walled guide sleeve 19 of circular-cylindrical cross section. A valve body 20 is received with a press fit in the guide sleeve 19, beginning at the receiving bore 15. The valve body 20 has a valve seat 21 for a closing member 22 of an armature 23 that can be moved longitudinally in the guide sleeve 19. On the end remote from the valve body 20, the guide sleeve 19 is closed by a magnet core 24 which is part of the valve dome 16. The magnet core 24 engages the inside of the guide sleeve 19 with a press fit, leaving an air gap 25 between it and the armature 23, and is joined to the guide sleeve by a weld 26 extending all the way around. This connection is pressure-tight and can withstand heavy hydraulic loads. A closing spring 27 engaging the magnet core 24 is received in the armature 23 and in the position of repose of the valve 10, as shown, keeps the closing member 22 in contact with the valve seat 21: Thus the valve 10 is closed when without current.

A bushing 29 is slipped onto the middle portion of the guide sleeve 19, specifically radially outside the magnetically operative armature 23. The bushing 29 has a wall thickness greater than that of the guide sleeve 19 of the valve dome 16. Counter to the valve body 20, the bushing 29 is provided with a radially protruding securing flange 30, both end faces 31 and 32 of which extend at right angles to the axis of the receiving bore 15, which is at the same time the longitudinal axis of the valve 10. The bushing 29 comprises magnetizable material, such as soft-magnetic steel. It is firmly joined to the stainless steel guide sleeve 19 by welding 33. The welding can be done, as shown, on the face end of the sleeve 29, or it may be located in the region of one or more recesses 34, with which the wall thickness of the bushing 29 is reduced in the region of the boundary plane 17. The welding 33 can encompass either the entire circumference of the guide sleeve 19 or only portions thereof. Instead of the welding 33, the connection of the bushing 29 to the guide sleeve 19 can also be done by adhesive bonding.

Beginning at the securing flange 30, a support ring 37 and a sealing ring 38, which tightly seals off the receiving bore 15 from the outside, are received on the portion of the guide sleeve 19 toward the receiving bore 15. The sealing ring 38 is followed by a filter sleeve 39, a second sealing ring 40, and a support ring 41. The second sealing ring 40 separates pressure fluid lines 42 and 43 of the valve block 11, the passage through which can be switched with the valve 10.

The dimensionally rigidly embodied securing flange 30 of the bushing 29 is received in a bore step 46 of the receiving bore 15. The original contour of the bore step 46 is represented by dot-dashed lines: Thus the diameter of the bore step is smaller than the diameter of the electric portion 14 of the valve 10. The end face 32 toward the valve body of the securing flange 30 rests on the bottom of the bore step 46. The other end face 31 of the securing flange 30 is conversely covered by a bead 47 of material which is made by caulking 48 of the material positively displaced from the edge of the bore. The region at the bore edge of the step 46 acted upon by this embossed connection is also located inside the diameter of the electric portion 14. The bead 47 of material engages the entire circumference of the securing flange 30 and secures the position of the hydraulic portion 13 in the valve block 11. It is capable of reliably diverting into the valve block 11 the forces that become operative inside and outside the hydraulic portion 13 and are transmitted to the securing flange 30. If the stress is not so great, it may suffice for only portions of the securing flange 30 to be engaged by portions of the material bead 47.

The electric portion 14 of the valve 10, once the hydraulic portion 13 has been secured in the valve block 11, is mounted on the valve dome 16 in the region of the magnetically operative elements, that is, the armature 33 and magnet core 24. The electric portion 14 has an electric coil 51, which encompasses the valve dome 16 in the region of the magnet core 24. A housing 52 of soft-magnetic material fits over the coil 51, and an annular disk 53 also of soft-magnetic material is pressed into the bottom of this housing. On the face end remote from the boundary plane 17 of the housing 52, connection pins 54 of the coil 51 are formed. The housing 52 of the electric portion 14 fits, preferably without play, over the magnet core 24 on the one hand and, with its annular disk 53, over the bushing 29 of the hydraulic portion 13 on the other. When the electric coil 51 is excited, the bushing 29, like the magnet core 24, housing 52 and annular disk 53, contributes to conducting the magnetic flux to the armature 23 of the hydraulic portion 13. The magnetically operative magnet core 24 shifts the armature 23 into the open position of the valve 10.

Figure 2:
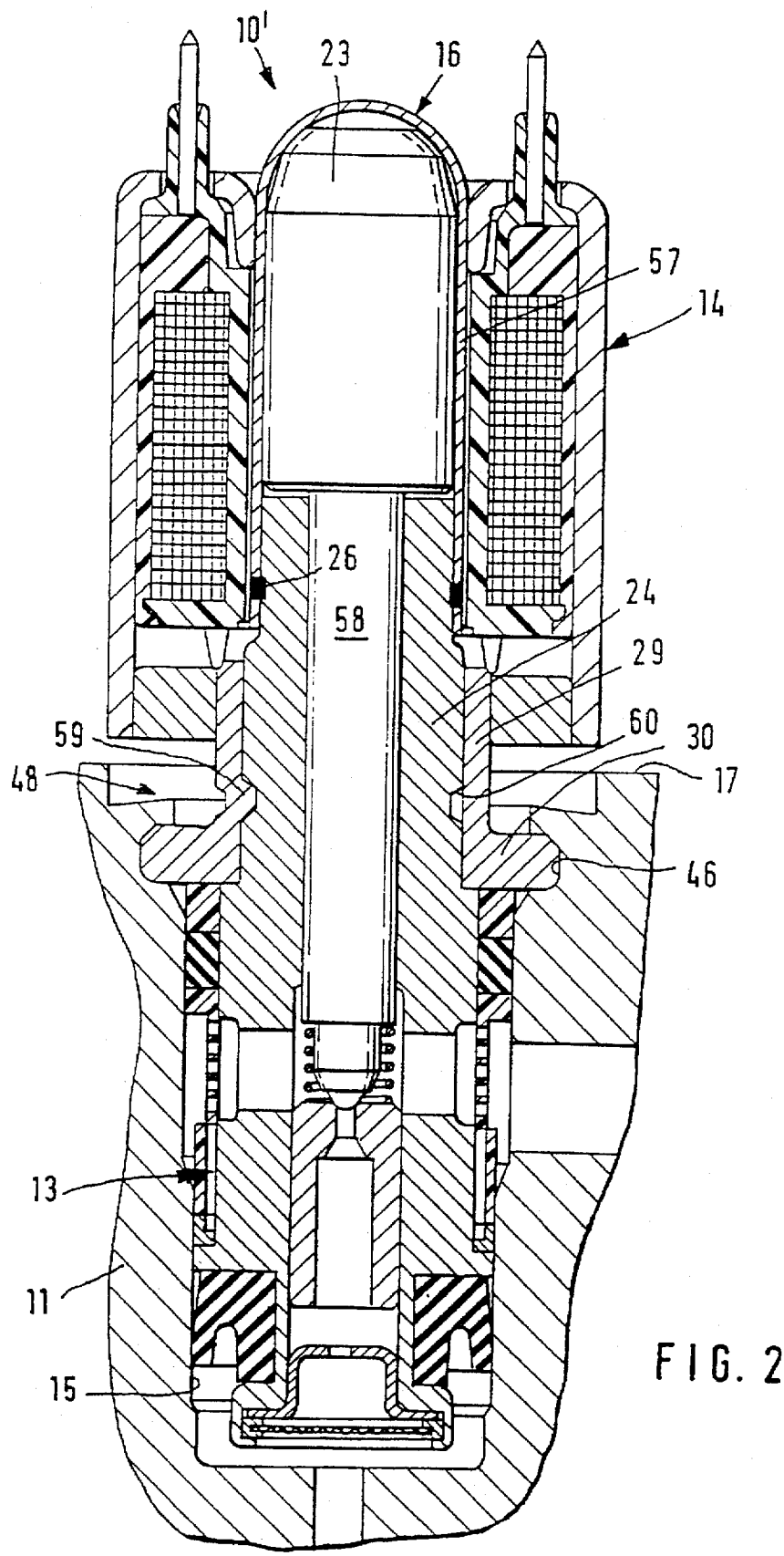

In the second exemplary embodiment shown in FIG. 2, the electromagnetically actuated valve 10' also has a hydraulic portion 13 and an electric portion 14. Because of its structural design, the valve 10 is switched to be open when without current in its current position of repose. It has a valve dome 16 with a thin-walled capsule 57, in which the armature 23 of the valve 10' is received in a longitudinally movable manner. The capsule 57 is joined by welding 26, analogously to the first exemplary embodiment, to the magnet core 24, which is elongated to inside the stepped receiving bore 15. The magnet core 24 penetrated by a valve tappet 58 has a relatively great wall thickness. In the region of the boundary plane 17 of the valve block 11, the bushing 29 is thrust, with its securing flange 30 received in the bore step 46, onto the magnetically operative magnet core 24. The connection of the bushing 29 to the magnet core 24 is attained by an embossed connection, and as a result embossed indentations 59 of the bushing engage a groove 60 or recesses of the magnet core 24. The securing flange 30 of the hydraulic portion 13 is joined to the valve block 11 by caulking 48, as in the first exemplary embodiment. Also in the same way as in that embodiment, the electric portion 14 is mounted on the valve dome 16 of the valve 10.

If there is a multiple assembly of valves 10 or 10' in the course of the boundary plane 11 of the valve block 11, a high packing density is attainable, since the caulking 48 is located inside the diameter of the electric portion 14. Valves 10 and 10' can therefore be disposed very close together.

What is claimed is:

1. A hydraulic unit (12) for traction-controlled motor vehicle brake systems, comprising
   a valve block (11) of a light metal with at least one stepped receiving bore (15) for a hydraulic portion (13) of an electromagnetically actuated valve (10), said hydraulic portion includes a thin walled guide sleeve (19),
   a bushing (29), said bushing (29) includes a securing flange (30), disposed on the thin walled guide sleeve (19) of the hydraulic portion (13), said bushing is inserted into said receiving bore (15) and includes a bottom surface which seats on a step (46) of the receiving bore (15) and is positionally secured by caulking (48) of the light metal of the valve block (11),
   a pressure-tight valve dome (16) is secured to said thin walled guide sleeve, said pressure-tight valve dome (16) contains magnetically operative elements including an armature (23) and a magnet core (24) of the hydraulic portion (13), and which in an extension of the receiving bore (15) said valve dome (16) extends beyond a boundary plane (17) of the valve block (11),
   and an electric-magnetic portion (14) of the valve (10) is mounted on and surrounds the valve dome (16), said electric-magnetic portion includes an electric coil (51) that surrounds the valve dome and the electric coil is surrounded by a magnetic flux-conducting housing (52) that conducts a magnetic flux to said armature.

2. A hydraulic unit of claim 1, in which the securing flange (30) protrudes radially from said bushing (29), which is firmly joined to the valve dome (16) and whose wall thickness is greater than that of a sleeve (19) that receives the magnetically operative elements of the valve dome (16).

3. A hydraulic unit of claim 2, in which the securing flange (30) has end faces (31, 32), extending at right angles to an axis of the receiving bore (15), of which one face (32) rests on the bore step (46) and the other face (31) is at least partially covered by a bead of material (47) positively displaced from an end of said valve block (11).

4. A hydraulic unit of claim 2, in which the bushing (29) comprises a magnetizable material, said bushing is disposed radially outside one of the magnetically operative elements, which includes an armature (23) and magnet core (24) of the hydraulic portion (13), and is at least indirectly engaged circumferentially by the magnetic flux-conducting housing (52) of the electric-magnetic portion (14) of the valve (10).

5. A hydraulic unit as set forth in claim 1, wherein the light metal is aluminum.

* * * * *